(12) United States Patent
Chaudhury et al.

(10) Patent No.: US 12,186,123 B2
(45) Date of Patent: Jan. 7, 2025

(54) POWER SUPPLY CIRCUIT FOR A COMPUTED TOMOGRAPHY SYSTEM

(71) Applicant: Siemens Healthcare GmbH, Erlangen (DE)

(72) Inventors: Shameem Kabir Chaudhury, Nuremberg (DE); Thomas Hilderscheid, Altdorf (DE); Bjoern Kreisler, Hausen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 233 days.

(21) Appl. No.: 18/155,895

(22) Filed: Jan. 18, 2023

(65) Prior Publication Data

US 2023/0225694 A1    Jul. 20, 2023

(30) Foreign Application Priority Data

Jan. 20, 2022 (DE) .............. 10 2022 200 649.6

(51) Int. Cl.
| | |
|---|---|
| *A61B 6/03* | (2006.01) |
| *A61B 6/00* | (2006.01) |
| *H02J 7/00* | (2006.01) |
| *H02J 7/34* | (2006.01) |
| *H02J 9/06* | (2006.01) |

(52) U.S. Cl.
CPC ............... *A61B 6/56* (2013.01); *A61B 6/032* (2013.01); *A61B 6/035* (2013.01); *H02J 7/0063* (2013.01); *H02J 7/345* (2013.01); *H02J 9/06* (2013.01); *H02J 9/061* (2013.01); *H02J 9/068* (2020.01);
(Continued)

(58) Field of Classification Search
CPC . A61B 6/032; A61B 6/035; A61B 6/56; H02J 7/0063; H02J 9/06; H02J 9/061; H02J 9/062; H02J 9/068; H02J 2207/50; H02J 2310/23
See application file for complete search history.

(56) References Cited

U.S. PATENT DOCUMENTS

| | | |
|---|---|---|
| 2012/0256099 A1 | 10/2012 | Allen et al. |
| 2017/0007197 A1 | 1/2017 | Beyerlein et al. |

(Continued)

FOREIGN PATENT DOCUMENTS

| | | |
|---|---|---|
| DE | 102014201805 A1 | 8/2015 |
| EP | 3795081 A1 | 3/2021 |

*Primary Examiner* — Mark R Gaworecki
(74) *Attorney, Agent, or Firm* — Harness, Dickey & Pierce, P.L.C.

(57) ABSTRACT

One or more example embodiments relates to a power supply circuit for a computed tomography system. The power supply circuit comprises a stationary power distributor including an uninterruptible power supply; a co-rotating bias voltage supply, the co-rotating bias voltage supply including a voltage supply input, a bias voltage supply output, and a bias voltage monitoring unit, the bias voltage monitoring unit being configured to activate or to deactivate the bias voltage supply output as a function of an electrical input voltage detected at the voltage supply input, and the bias voltage includes a sensor configure to detect the electrical input voltage at the voltage supply input; and an auxiliary voltage source having a power buffer, the power buffer configured to supply the bias voltage monitoring unit with electrical power for deactivation of the bias voltage supply output.

20 Claims, 3 Drawing Sheets

(52) U.S. Cl.
CPC ........... *H02J 9/062* (2013.01); *H02J 2207/50* (2020.01); *H02J 2310/23* (2020.01)

(56) References Cited

U.S. PATENT DOCUMENTS

2017/0085122 A1* 3/2017 Nasiri ...................... A61B 6/56
2021/0085278 A1 3/2021 Chaudhury et al.

* cited by examiner

POWER SUPPLY CIRCUIT FOR A COMPUTED TOMOGRAPHY SYSTEM

CROSS-REFERENCE TO RELATED APPLICATION(S)

The present application claims priority under 35 U.S.C. § 119 to German Patent Application No. 10 2022 200 649.6, filed Jan. 20, 2022, the entire contents of which are incorporated herein by reference.

FIELD

One or more example embodiments of the present invention relates to a power supply circuit for a computed tomography system. Furthermore, one or more example embodiments of the present invention relates to a computed tomography system. One or more example embodiments of the present invention relates, moreover, to a method for operating a computed tomography system.

STATE OF THE ART

Computed tomography systems, CT systems for short, are used for medical imaging examination of patients. An examination region is subjected by way of an X-ray source, which is attached to a rotating part of the CT system, to X-ray radiation from different directions and the attenuated X-ray radiation is detected via a co-rotating X-ray detector or count rate detector.

The new generation of photon counting detectors of CT systems requires a continuous supply of an electrical bias voltage. For this purpose, the CT system comprises a power supply circuit having what is known as a bias voltage supply, which co-rotates with the rotating functional elements of the CT system, therefore in particular of the X-ray source and the X-ray detector, and receives power from a stationary power distributor via a power transmission path and supplies the functional elements with a bias voltage.

If the bias voltage is interrupted, the X-ray detector needs a long time, that is to say, several hours, to regain its thermal equilibrium. Calibration processes have to take place after each replacement of the X-ray source, therefore. By way of example, an entire operating day is required for replacement of an X-ray source, and this is time-consuming and expensive.

If a power failure occurs in the grid, the bias voltage of the X-ray detector cannot be maintained without additional protective measures, and this results in the problems already mentioned.

It is customary therefore to fit the stationary part of a CT system with an additional uninterruptible power supply (abbreviated to UPS) in the stationary part of the CT system. An arrangement of this kind is described in EP 3 795 081 A1. In the case of a power failure caused by the grid, it is thus possible to change over to the uninterruptible power supply, for example a battery or an accumulator. Changing over lasts less than a second, for example 150 ms. No electrical power is available to the bias voltage supply from the stationary side during this short time interval.

It is possible to bridge said changeover time by way of additional measures. For example, the bias voltage supply can be supplemented by an internal power buffer. The power buffer in the bias voltage supply supplies the required power during the changeover time to maintain the bias voltage at the output of the bias voltage supply. In this way an interruption to the bias voltage during the changeover is avoided at the output of the bias voltage supply. A circuit of this kind is demonstrated in FIG. 1. However, this kind of direct buffering of the bias voltage is space- and time-consuming since the bias voltage supply requires a high power, for example up to 1,000 watts. By way of example, capacitors with large dimensions are required to store sufficient power in order to maintain the bias voltage.

SUMMARY

One or more example embodiments of the present invention provide a power supply circuit of a computed tomography system that has resistance to power failures and requires fewer resources.

One or more example embodiments relates to a power supply circuit for a computed tomography system. The power supply circuit comprises a stationary power distributor including an uninterruptible power supply; a co-rotating bias voltage supply, the co-rotating bias voltage supply including a voltage supply input, a bias voltage supply output, and a bias voltage monitoring unit, the bias voltage monitoring unit being configured to activate or to deactivate the bias voltage supply output as a function of an electrical input voltage detected at the voltage supply input, and the bias voltage includes a sensor configure to detect the electrical input voltage at the voltage supply input; and an auxiliary voltage source having a power buffer, the power buffer configured to supply the bias voltage monitoring unit with electrical power for deactivation of the bias voltage supply output.

According to one or more example embodiments, the bias voltage monitoring unit is configured to deactivate the bias voltage supply output in response to the sensor detecting the electrical input voltage undershoots a predetermined threshold voltage, and activate the bias voltage supply output in response to the sensor detecting that the electrical input voltage overshoots the predetermined threshold voltage.

According to one or more example embodiments, the bias voltage monitoring unit includes a non-volatile data memory storing information, the information indicating a duration the electrical input voltage undershoots a predetermined threshold voltage.

According to one or more example embodiments, the bias voltage monitoring unit includes a time measuring unit, the time measuring unit configured to ascertain a duration the electrical input voltage undershoots a predetermined threshold value of an electrical voltage.

According to one or more example embodiments, the time measuring unit includes a clock cycle counting unit, the clock cycle counting unit configured to ascertain the duration by counting clock cycles.

According to one or more example embodiments, the bias voltage monitoring unit includes a write unit, the write unit configured to write the duration into a non-volatile data memory.

According to one or more example embodiments, the bias voltage monitoring unit is configured to activate the bias voltage supply output when the electrical input voltage reaches the predetermined threshold value of an electrical voltage before the duration reaches a predetermined maximum value, and activate a standard process for initializing and booting up the electrical bias voltage supply output when the input voltage does not reach the predetermined threshold value of an electrical voltage before the duration reaches a predetermined maximum value.

According to one or more example embodiments, the standard process for initializing and booting up the electrical bias voltage supply output comprises a controlled booting up of the electrical bias voltage.

According to one or more example embodiments, the bias voltage monitoring unit is configured to continue to ascertain the duration and to write a value of the duration into the non-volatile data memory as long as sufficient power is supplied by the power buffer when it is detected that the electrical input voltage does not reach a predetermined threshold value before the duration reaches a predetermined maximum value.

According to one or more example embodiments, the bias voltage monitoring unit includes a read-out unit, the read-out unit configured to read out a value of the duration to ascertain a power storage capacity of the power buffer.

According to one or more example embodiments, the bias voltage monitoring unit is configured to delete the non-volatile data memory after the read out.

According to one or more example embodiments, the power buffer comprises an electrical capacitor as a power storage unit.

According to one or more example embodiments, a computed tomography system includes a scanning unit configured to acquire raw data from a patient with a semiconductor detector; a control facility for actuating the scanning unit; and the power supply circuit according to one or more example embodiments.

According to one or more example embodiments, a method for operating a computed tomography system includes detecting an electrical input voltage at a voltage supply input of a co-rotating bias voltage supply of the computed tomography system by a bias voltage monitoring unit; activating or deactivating a bias voltage supply output of the bias voltage supply as a function of the electrical input voltage detected at the voltage supply input; and supplying the bias voltage monitoring unit with electrical power by an auxiliary voltage source having a power buffer for the deactivating of the bias voltage supply output.

BRIEF DESCRIPTION OF THE DRAWINGS

The invention will be explained once again in more detail below on the basis of exemplary embodiments and with reference to the accompanying figures. Identical components are provided with identical reference numerals in the different figures.

As a rule, the figures are not to scale. In the drawings.

DETAILED DESCRIPTION

Figure 1:
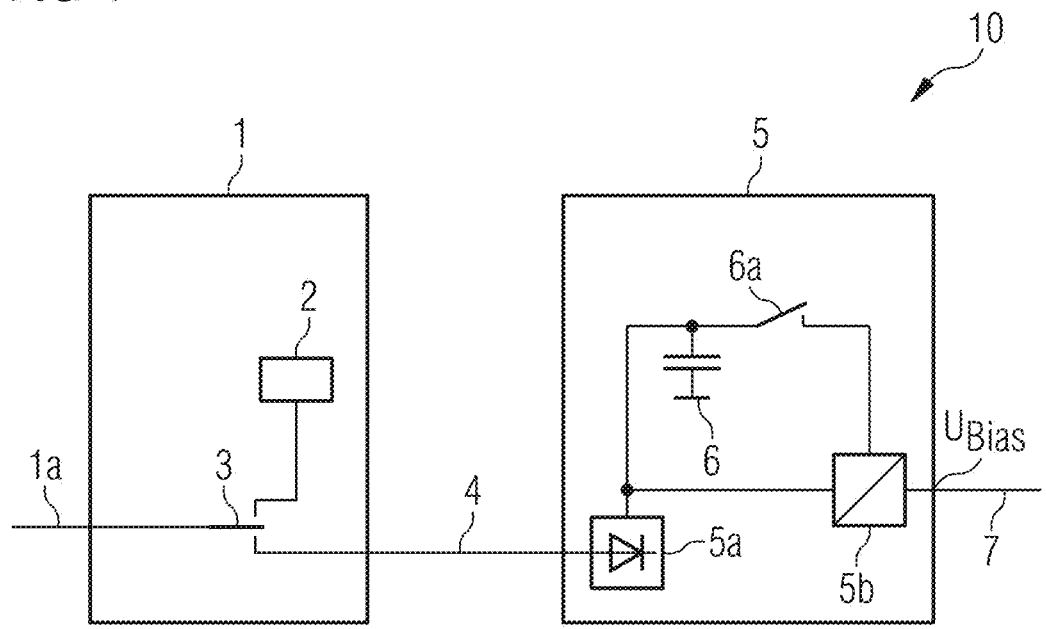
FIG. 1 schematically shows a power supply circuit of a CT system according to an exemplary embodiment.

An inventive power supply circuit for a CT system has a stationary power distributor and a rotating part with a scanning function having an X-ray detector and an X-ray source. A stationary power distributor of this kind receives electrical current from a stationary grid and distributes it and transfers the electrical current to a bias voltage supply co-rotating with the rotating part of the CT system and which is likewise part of an inventive power supply circuit. The bias voltage supply serves to convert the electrical current received from the stationary power distributor into direct current having a predetermined electrical bias voltage and to supply the X-ray detector or the modules of the X-ray detector of the CT system with the electrical bias voltage. For this purpose, the bias voltage supply can comprise a rectifier and a voltage converter connected downstream.

The stationary power distributor comprises an uninterruptible power supply. The uninterruptible power supply is adapted as a substitute to continuously supply current in the event of a grid failure. An uninterruptible power supply of this kind can comprise for example a battery or an accumulator. To change between the grid and the uninterruptible power supply, the stationary power distributor can comprise a changeover unit for changing over between a grid supply and the uninterruptible power supply.

The co-rotating bias voltage supply already mentioned comprises a voltage supply input for receiving electrical power via a power transmission path between the stationary power distributor and the bias voltage supply.

The bias voltage supply also comprises a bias voltage supply output and bias voltage monitoring unit. The bias voltage monitoring unit comprises a sensor, preferably a voltage sensor, for detecting an electrical input voltage at the voltage supply input and is adapted to activate or deactivate the bias voltage supply output as a function of the electrical input voltage detected at the voltage supply input. Activation or deactivation can take place via an activation or deactivation of the voltage converter already mentioned. A switching command can be given for this purpose. As an alternative possible implementation, a switch configured as hardware can also be used for activation/deactivation.

An auxiliary voltage source having a power buffer for supplying the bias voltage monitoring unit with electrical power for the case of deactivation of the bias voltage supply output is also part of the co-rotating bias voltage supply. As only the power which is necessary for the power supply or supplying the bias voltage monitoring unit with an auxiliary voltage during the changeover between the different power sources, that is to say, between the grid and the uninterruptible power supply, is stored, less power has to be stored as buffer power than in the case of the possible approach outlined in the introduction in which the bias voltage for the X-ray detector is maintained by a power buffer with much larger dimensions. Advantageously, capacitors with smaller dimensions can be used for the power buffer of the auxiliary voltage source, whereby it is possible to save space and resources. Particularly advantageously, a controlled activation and deactivation of the bias voltage generated by the bias voltage supply now prevents an uncontrolled change in the bias voltage. Since the load hanging on the bias voltage behaves capacitively, uncontrolled booting up or shutting down of the bias voltage would potentially result in an excessive current. The strong current could prove to be a safety problem for maintenance personnel, operators or patients. Furthermore, such a strong switch-on current or switch-off current would increase the wear on the connected elements or endanger the functioning thereof. Advantageously, the buffered bias voltage monitoring unit therefore means that the electrical currents generated by the bias voltage supply do not constitute an excessive strain even in the case of a changeover between different power sources for the elements connected downstream, and the consumption of power and resources is simultaneously reduced owing to the reduced power requirement for power buffering of the bias voltage monitoring unit. By way of example, the bias voltage monitoring unit requires only a few watts of power in contrast to a very high power consumption of up to 1,000 watts for maintaining the bias voltage.

According to an example embodiment, a computed tomography system has a scanning unit for acquiring raw data from a patient with an X-ray detector, which comprises semiconductor material. According to an example embodiment, the computed tomography system also has a control facility for actuating the scanning unit and an inventive power supply circuit. The computed tomography system shares the advantages of the power supply circuit.

According to an example embodiment, a method for operating a computed tomography system, an electrical input voltage is detected at the voltage supply input of a co-rotating bias voltage supply of the computed tomography system by way of a bias voltage monitoring unit. Furthermore, a bias voltage supply output of the bias voltage supply is activated or deactivated as a function of the electrical input voltage detected at the voltage supply input. For the case of a deactivation of the bias voltage supply output, the bias voltage monitoring unit is supplied with electrical power by an auxiliary voltage source having a power buffer. While the bias voltage at the bias voltage supply output of the bias voltage supply may not be maintained with the power of the auxiliary voltage source, this power is sufficient to maintain the monitoring and control of the bias voltage by the bias voltage monitoring unit even if no or insufficient electrical voltage is applied at the input of the bias voltage supply. Advantageously, operation of the CT system is resource-saving compared to operation of a conventional CT system and uncontrolled behavior of the CT system is prevented nevertheless.

Further, particularly advantageous embodiments and developments of the invention can be found in the dependent claims and the following description, it being possible for the claims of one category to also be developed analogously to the claims and descriptive parts relating to another category of claims and in particular for individual features of different exemplary embodiments or variants to be combined to form new exemplary embodiments or variants.

In one variant of the power supply circuit, the bias voltage monitoring unit is adapted to deactivate the bias voltage supply output for the case where the sensor, preferably a voltage sensor, detects that the electrical input voltage undershoots a predetermined threshold voltage. Furthermore, the bias voltage monitoring unit is adapted to activate the bias voltage supply output for the case where the sensor detects that the electrical input voltage overshoots the predetermined threshold voltage. By measuring an undershooting or overshooting of a predetermined threshold voltage, a period is ascertained in which a changeover takes place between different power sources. Advantageously, in this timeframe the power supply of the bias voltage monitoring unit is buffered with a comparatively small power storage unit, so the bias voltage can then be restored in a controlled manner, controlled by the still active bias voltage monitoring unit.

In one embodiment of the power supply circuit, the bias voltage monitoring unit comprises a non-volatile data memory, which is adapted to store information, which indicates for which duration the bias voltage supply output is deactivated or for which duration the electrical input voltage at the voltage supply input of the bias voltage supply undershoots a predetermined threshold voltage. Advantageously, the ascertained duration can be used as a basis for the selection of the subsequent activation process of the bias voltage supply output.

In one variant of the power supply circuit, the bias voltage monitoring unit comprises a time measuring unit, which is adapted to ascertain the duration during which the electrical input voltage at the voltage supply input of the bias voltage supply undershoots a predetermined value of a threshold voltage. Advantageously, knowledge of the duration of the deactivation of the bias voltage supply output necessary for the decision with regard to a suitable activation process of the bias voltage supply output can be imparted by this time measuring unit.

Preferably, the time measuring unit of the power supply circuit comprises a clock cycle counting unit, which is adapted to ascertain the elapsed duration by counting clock cycles. Clock cycles should here be taken to mean clock signals or clock sequences controlled thereby with which the correct sequence of operation over time of an electronic circuit is ensured. Preferably, the clock signals are periodic signals with which time can be measured very easily. Advantageously, clock cycles, for example the clock cycles with which the bias voltage monitoring unit is operated, can be used as a measure of time for ascertaining the duration of the deactivation of the bias voltage supply output.

The bias voltage monitoring unit preferably also comprises a write unit, which is adapted to write the ascertained duration into the non-volatile data memory. Advantageously, the ascertained duration can be used at a later instant for monitoring the functionality of the power buffer. If the power buffer no longer has sufficient storage capacity, the stored duration has a lower value than a predetermined threshold value. If the stored duration is read from the non-volatile data memory, then on this basis it is possible to decide whether the power buffer should be replaced to ensure the functionality of the bias voltage monitoring unit.

The bias voltage monitoring unit of the power supply circuit is preferably adapted to immediately activate the bias voltage supply output for the case where it is detected that the input voltage at the voltage supply input of the bias voltage supply reaches the predetermined threshold value of an electrical voltage before the elapsed duration reaches a predetermined maximum value. Advantageously, with only a very short interruption to the bias voltage, it is possible for it to be applied directly again at the bias voltage supply output since in this case it should be assumed that the functional elements of the CT system loaded by the bias voltage, such as the X-ray detector, have not yet come out of thermal equilibrium and can be directly supplied with the bias voltage again, therefore. A typical value for the maximum value can be for example 0.2 seconds or 0.5 seconds.

Furthermore, the bias voltage monitoring unit is adapted to activate a standard process for initializing and booting up the electrical bias voltage for the case where it is detected that the input voltage does not reach the predetermined threshold value of an electrical voltage before the elapsed duration reaches the predetermined maximum value. Advantageously, for the case where, owing to the longer duration during which the functional units of the CT system were not supplied with the bias voltage, these functional units are no longer in thermal and electrodynamic equilibrium, a predefined gradual booting up of these units is carried out to prevent an excessive switch-on current and in order to not damage these units. A standard process of this kind, also referred to as a bootup process, comprises an initialization of individual elements of a scanning unit or checking the functional readiness of the elements by way of a notification procedure and an incremental switching on of these elements.

For this, the bias voltage monitoring unit can comprise a clock cycle counter and, for the case where it is detected that the input voltage at the voltage supply input of the bias voltage supply has still not reached the predetermined threshold value, can be adapted to begin to count clock cycles, and to write one value respectively into a non-volatile data memory for the counted clock cycles. Furthermore, the bias voltage monitoring unit is adapted to immediately activate the bias voltage supply output for the case where the input voltage reaches the predetermined threshold value again before a predetermined number of clock cycles were counted, and to activate a standard process for initializing and booting up the electrical bias voltage for the case where the input voltage does not reach the predetermined threshold value before said predetermined number of clock cycles was counted. Advantageously in this variant the number of clock cycles of the bias voltage monitoring unit can be used as a measure of the duration of the suspension of the supply voltage.

In contrast to the direct switching on or activating of the bias voltage, said standard process does not take place instantaneously but over a longer period of several minutes and for initializing and booting up the electrical bias voltage customarily comprises an incremental or controlled relatively slow booting up of the electrical bias voltage. Advantageously, the functionality of individual components, in particular of the X-ray detector, is interrogated in such a standard process. This prevents the X-ray detector from being operated in a non-ready state and potentially being damaged as a result.

Preferably, the bias voltage monitoring unit of the power supply circuit is adapted to continue to ascertain the elapsed duration for the case where it is detected that the input voltage does not reach the predetermined threshold value before the elapsed duration reaches a predetermined maximum value, and to write the value of the elapsed duration into the non-volatile data memory as long as there is sufficient power available for this from the power buffer.

If a minimum number or the number of clock cycles corresponding to the predetermined maximum value of an elapsed duration was counted, therefore, the bias voltage monitoring unit is adapted to continue to write the number of clock cycles into the non-volatile data memory as long as there is sufficient power available for this from the power buffer. While it is now already clear that a standard process for initializing and booting up the electrical bias voltage has to be used during subsequent activating of the bias voltage supply output, knowledge of the number of counted clock cycles can provide information about the storage capacity of the power buffer of the bias voltage monitoring unit.

For this purpose, the bias voltage monitoring unit of the power supply circuit can also have a read-out unit for reading out the non-volatile data memory to read out a value of an elapsed duration to ascertain the power storage capacity of the power buffer and/or optionally to ascertain whether the power storage capacity of the power buffer has been reduced and/or whether the power storage capacity is possibly still sufficient. For this purpose, the ascertained duration can be compared with a threshold value or reference value.

The bias voltage monitoring unit can be adapted to delete the non-volatile data memory after a reading-out process. Advantageously, the non-volatile data memory can be directly written to again with incremental values in the case of a renewed changeover between different power sources.

The power buffer of the power supply circuit can comprise for example an electrical capacitor as a power storage unit. Alternatively, an accumulator can also be used as a power buffer. As already mentioned, the power buffer, for example a capacitor, can have smaller dimensions than in the case of a direct buffering of the bias voltage supply output using a power buffer.

FIG. 1 schematically shows a power supply circuit 10 of a CT system (not shown) having an internal power buffer for maintaining a generated bias voltage during a changeover process between different power sources, as briefly mentioned in the introduction to the description. The power supply circuit 10 comprises a stationary power distributor 1 shown on the left side of the image in FIG. 1 and a rotating bias voltage supply 5, shown on the right side of the image in FIG. 1, which is arranged on the rotating part of the CT system (see FIG. 5), which is also referred to as a ring mount. The power distributor 1 comprises a grid connection 1a or grid input terminal, which is shown in FIG. 1 on the left side of the drawing. The grid connection 1a is electrically connected to a changeover switch 3, which is likewise part of the power distributor 1. With the changeover switch 3 it is possible to change over between the grid connection 1a and an uninterruptible power supply 2, for example an accumulator, which is likewise part of the stationary power distributor 1.

The power distributor 1 is electrically connected to the bias voltage supply 5 via a power transmission path 4. A collector ring (not shown) is embodied at the stationary side as a power transfer facility as part of the power transmission path 4, and this can be electrically contacted by this rotating part via brushes (not shown) of the rotating part.

The bias voltage supply 5 has a rectifier 5a, which converts the grid current supplied as alternating current into direct current. In addition, the bias voltage supply 5 comprises a voltage converter 5b, with which a suitable electrical bias voltage or a predetermined value of the electrical bias voltage is generated at a bias voltage supply output 7 of the bias voltage supply 5. The generated electrical bias voltage is provided to an X-ray detector of the CT system (not shown in FIG. 1).

An internal power buffer 6 having a capacitor as a physical power storage unit, which can be electrically connected to the bias voltage supply output 7 and be disconnected from it via a switch 6a, is also part of the bias voltage supply 5. If there is a power failure in the grid, there is a changeover to the uninterruptible power supply 2 in the power distributor 1 by way of the changeover switch 3. So that there is no drop in bias voltage UBias at the bias voltage supply output 7 of the bias voltage supply 5 during the short changeover time, the required power is supplied from the internal power buffer 6 of the bias voltage supply 5 to the bias voltage supply output 7 during the changeover time. As already mentioned, the internal power buffer 6 has to have relatively large dimensions to be able to provide the required power for the functional elements on the ring mount.

Figure 2:
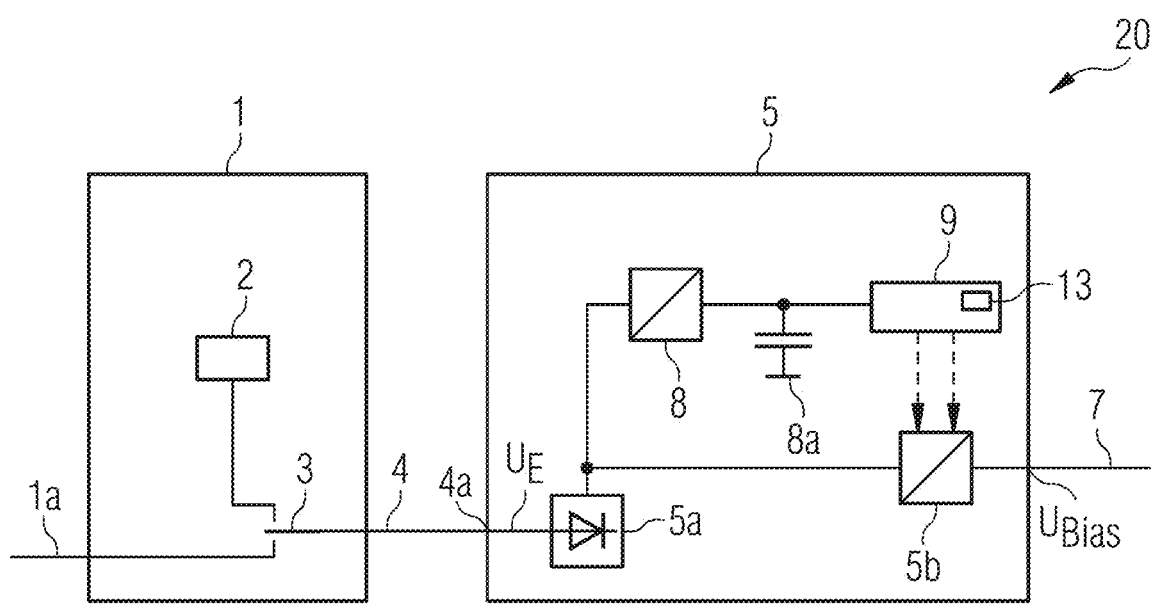
FIG. 2 shows a schematic representation of a power supply circuit of a CT system according to one exemplary embodiment of the invention.

FIG. 2 shows a schematic representation of a power supply circuit 20 of a CT system according to a first exemplary embodiment of the invention. The power supply circuit 20 shown in FIG. 2 differs from the power supply circuit 10 shown in FIG. 1 in that instead of an internal power buffer 6 for the bias voltage supply output 7, a bias voltage monitoring unit 9 for monitoring an input voltage UE at a voltage supply input 4a of the bias voltage supply 5 and for controlling the voltage converter 5b is embodied in the bias voltage supply 5. For this purpose, bias voltage monitoring unit 9 comprises as a sensor a voltage sensor (not shown), which is arranged at the input 4a. Furthermore, the bias voltage supply 5, unlike in FIG. 1, comprises an auxiliary voltage converter unit 8 and a capacitor 8a as a power buffer for storing auxiliary power or as an auxiliary voltage source for the bias voltage monitoring unit 9. If there is a power failure in the grid, there is a changeover to the uninterruptible power supply 2 in the power distributor 1 by way of the changeover switch 3.

During the changeover time the bias voltage monitoring unit 9 deactivates the bias voltage supply output 7 by a deactivation of the voltage converter 5b. The bias voltage monitoring unit 9 then measures the input voltage at the voltage supply input 4a of the bias voltage supply 5 and it counts the number of clock cycles which elapse until a sufficient input voltage UE is applied at the voltage supply input 4a of the bias voltage supply 5. The bias voltage monitoring unit 9 receives electrical power from the capacitor 8a for this process. If the bias voltage monitoring unit 9 detects that the entire input voltage UE is applied at the voltage supply input 4a of the bias voltage supply 5 again, the bias voltage monitoring unit 9 activates the bias voltage supply output 7 or the voltage converter 5b, so the original bias voltage UBias is directly applied again at the bias voltage supply output 7. The type of activation depends on the number of ascertained clock cycles. If a predetermined number of clock cycles is not overshot, the bias voltage supply output 7 is directly activated by the bias voltage monitoring unit 9 without delay. If the number of counted clock cycles overshoots said predetermined number on the other hand, the bias voltage monitoring unit has to activate a time-consuming standard bootup procedure for generating the bias voltage UBias with incremental booting up of individual components. The ascertained clock cycles can be stored in a data memory 13 and used for monitoring the functionality of the power buffer.

Figure 3:
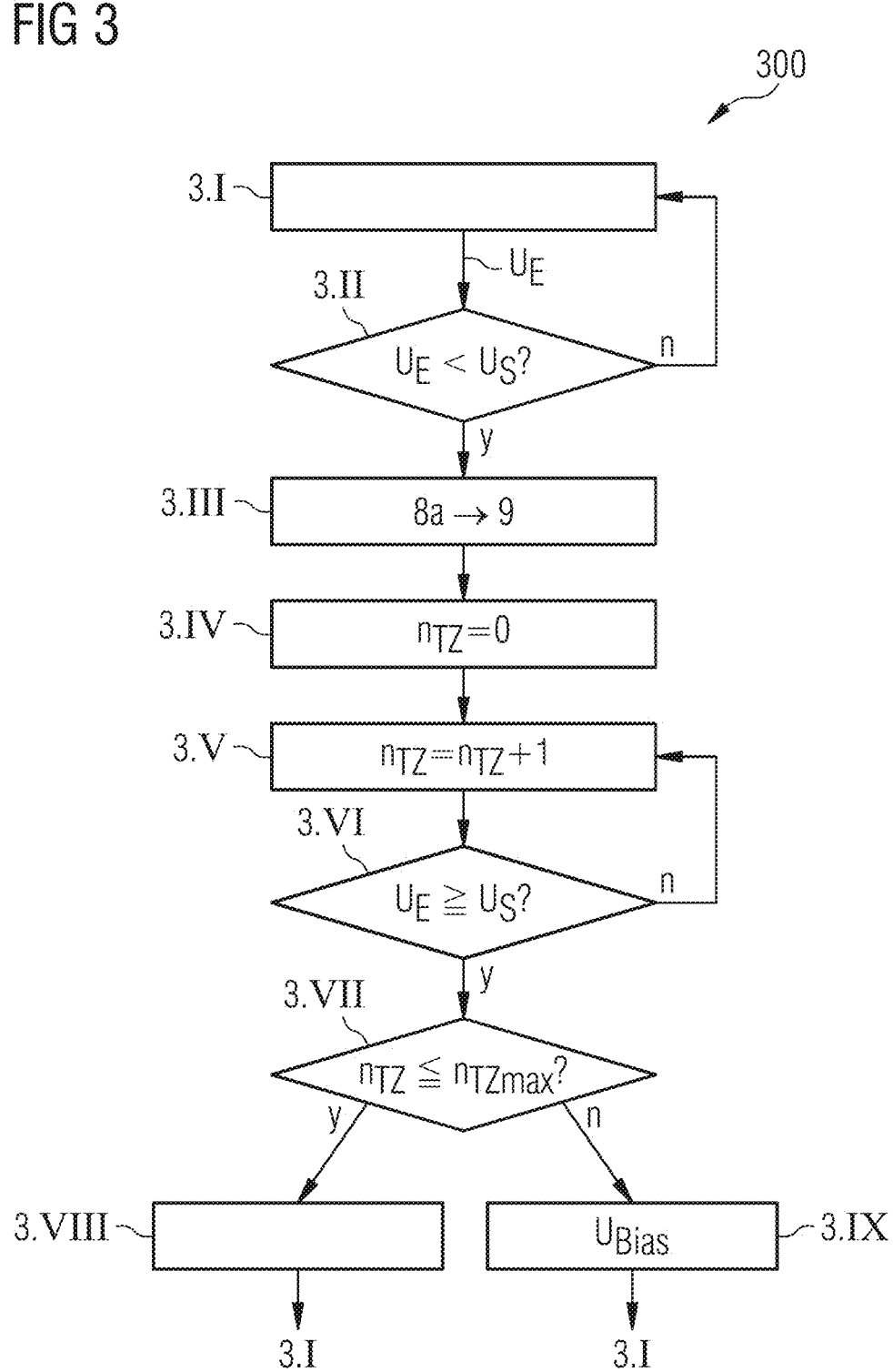
FIG. 3 shows a flowchart, which illustrates a method for operating a power supply circuit for a CT system according to one exemplary embodiment of the invention.

FIG. 3 shows a flowchart 300, which illustrates a method for safe operation of an inventive CT system according to one exemplary embodiment of the invention. The method comprises the following steps:

In step 3.I an electrical input voltage UE is detected at the voltage supply input 4a of a co-rotating bias voltage supply 5 of a CT system by a bias voltage monitoring unit 9. In step 3.II it is ascertained whether the electrical input voltage UE undershoots or overshoots a predetermined threshold voltage US. For the case where the predetermined threshold voltage US is undershot, and this is marked by "y" in FIG. 3, the method skips to step 3.III. For the case where the predetermined threshold voltage US is overshot, and this is marked by "n" in FIG. 3, the method returns to step 3.I.

In step 3.III the bias voltage supply output 7 is deactivated and the bias voltage monitoring unit 9 is supplied with electrical power by a capacitor 8a operating as a power buffer.

In step 3.IV a non-volatile data memory is deleted or the value of the number nTZ of counted clock cycles is set to the value "0" and counting of a number nTZ of clock cycles is started.

In step 3.V, after each counted clock cycle, a value is written into a non-volatile data memory, which increments the value of the number of counted clock cycles stored there by the value "1".

In step 3.VI a voltage sensor detects whether the electrical input voltage UE reaches the predetermined threshold voltage US again or even overshoots it. It is thereby ascertained in principle whether the changeover process between the two power sources has ended.

For the case where the predetermined threshold voltage US is reached or overshot, and this is marked by "y" in FIG. 3, the method skips to step 3.VII. For the case where the predetermined threshold voltage US is still being undershot, and this is marked by "n" in FIG. 3, the method returns to step 3.V.

In step 3.VII the non-volatile data memory is read out and it is ascertained whether the readout value nTZ of the counted clock cycles overshoots a predetermined value of a maximum number nTZmax. If this maximum number nTZmax is not overshot, and this is marked by "y" in FIG. 3, the method skips to step 3.VIII. If the maximum number nTZmax is overshot, and this is marked by "n" in FIG. 3, the method skips to step 3.IX. The maximum number nTZmax of clock cycles represents a numerical value, which corresponds to a time interval, which is still just short enough that the functional units of the rotating part of the CT system can be immediately operated without time-consuming warming up.

In step 3.VIII, owing to the short interruption time, for example 150 ms, which is represented by the low number of counted clock cycles, the bias voltage supply output 7 is immediately activated, and in addition the value of the number of clock cycles in the data memory of the bias voltage monitoring unit 9 is set to the value "0", so during the next interruption to the grid supply, incrementing the number of clock cycles starts at the value "0" again.

In step 3.IX on the other hand, owing to the long interruption time, a standard process for initializing and booting up the electrical bias voltage UBias is activated to prevent damage to the system.

The method then returns to step 3.I.

Figure 4:
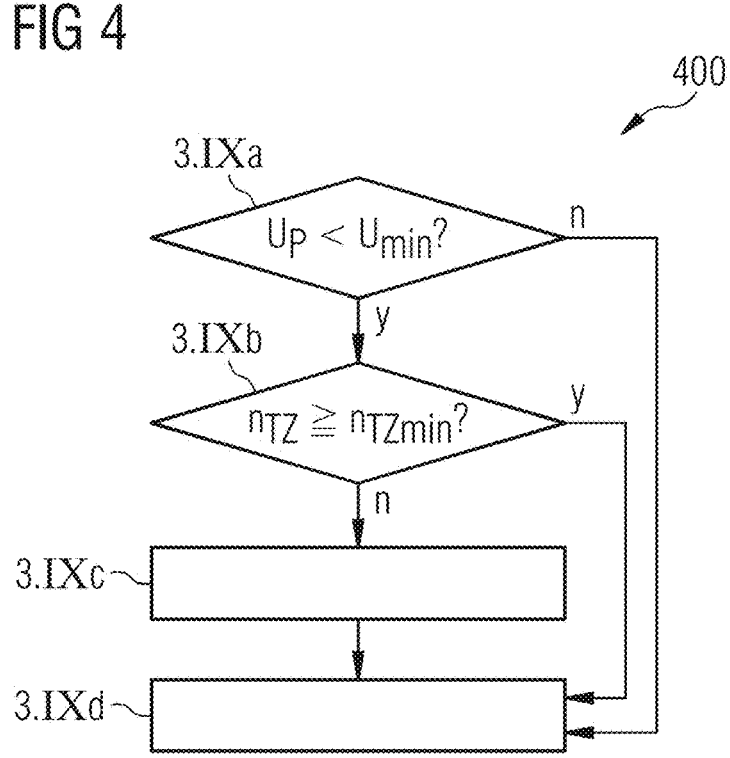
FIG. 4 shows a flowchart, which illustrates an optional procedure for ascertaining the functionality of a power buffer of an inventive power supply circuit.

FIG. 4 shows a flowchart 400, which shows an optional step sequence by which the method demonstrated in FIG. 3 can be supplemented. The optional step sequence relates to sub-steps of the step 3.IX demonstrated in FIG. 3. Step 3. IX relates to the branch of the method in which it was ascertained that the interruption in the bias voltage lasted too long. In this case, the number of clock cycles then continues to be counted until either the required input voltage UE is applied at the input again or until the required auxiliary voltage or a required minimum voltage Umin is no longer available for the bias voltage monitoring unit 9 owing to the discharge process of the capacitor 8a operating as a power buffer and therefore the bias voltage monitoring unit 9 can no longer continue to operate. In step 3.IXa it is ascertained whether the electrical voltage UP of the power buffer has a minimum voltage Umin. If the electrical voltage UP lies below the minimum voltage Umin, and this is marked by "y" in FIG. 4, the method skips to step 3.IXb, otherwise, and this is marked by "n" in FIG. 4, the method skips to step 3.IXd. In step 3.IXb it is ascertained whether the number nTZ of counted clock cycles TZ reaches or overshoots a minimum nTZmin. A minimum power storage capacity of the power buffer corresponds to the minimum nTZmin.

For the case where the minimum power storage capacity is reached, and this is marked by "y" in FIG. 4, the method skips to step 3.IXd in which the data memory, which stores the number of counted clock cycles, is set to the value "0" and a standard bootup procedure is triggered.

For the case where the minimum power storage capacity is not reached, and this is marked by "n" in FIG. 4, the method skips to step 3.IXc in which a replacement of the power buffer is carried out or planned/recommended. The method then skips to step 3.IXd and a standard bootup procedure is likewise triggered.

Figure 5:
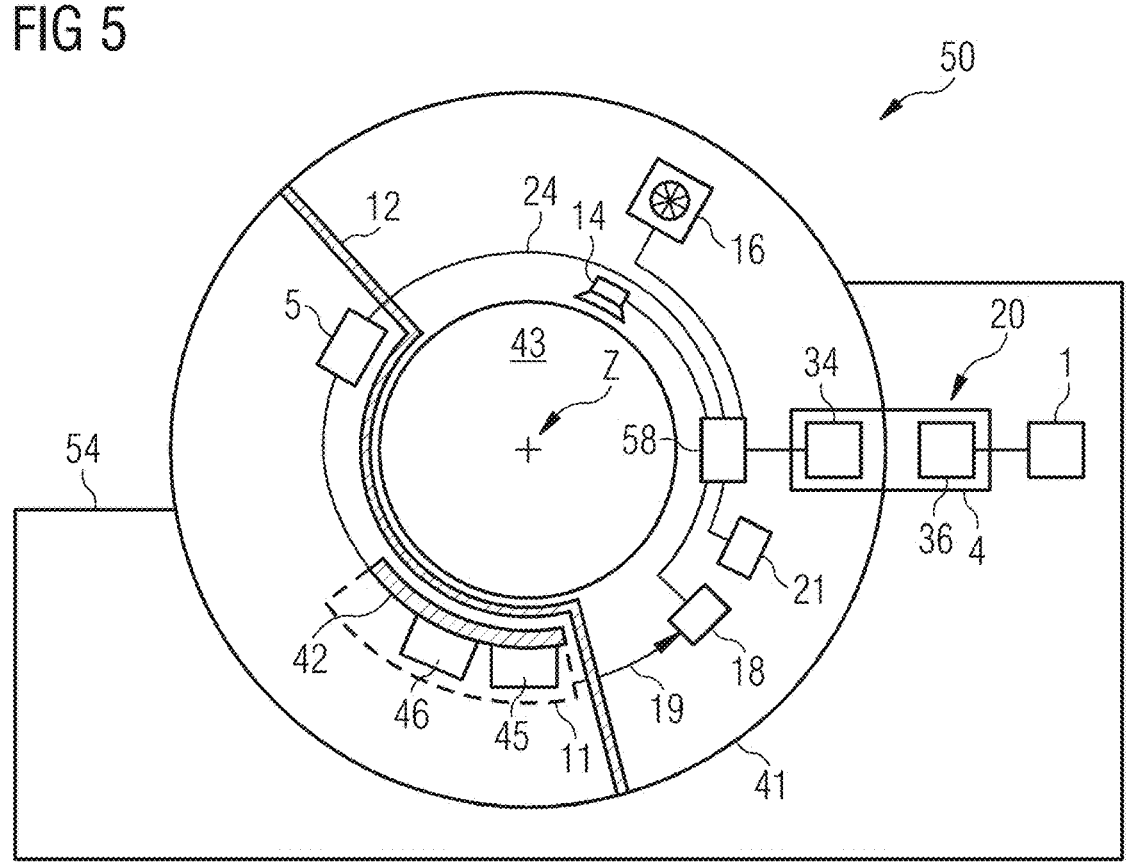
FIG. 5 shows a schematic representation of a CT system according to one exemplary embodiment of the invention.

FIG. 5 schematically represents a cross-section of a CT system 50. The CT system 50 comprises a ring mount 41 as a moving part and a holding frame 54 as a static part. In respect of the holding frame 54, the ring mount 41 is mounted to rotate about an axis z perpendicular to the image plane in the center of the ring mount 41. An X-ray detector 11 in an electrical insulation 12 is arranged on the ring mount 41.

An X-ray source 14, a fan 16, an image processing 18 and an electronic control device 21 are also conductively connected on the ring mount 41 to a voltage supply 58 acting as a central current distributor, from which voltage supply a line 24 also leads for supplying the X-ray detector 11. The image processing 18 is connected to the X-ray detector 11 by an optical signal cable 19. A rotating anode, including drive, a cathode heater and a cooler are also arranged (not shown) in the X-ray source 14. The voltage supply 58 functioning as a central current distributor is connected to a power transmission path 4, which has a power-absorbing component 34, which conducts power to the voltage supply 58.

A power-emitting component 36, arranged on the holding frame 54, of the power transmission path 4 is connected to a first power source, which can be provided by a power distributor 1 having a grid connection. The power distributor 1, the power transmission path 4 and a bias voltage supply 5 arranged between the voltage supply 58 and the X-ray detector 11, together with the corresponding connecting wires, form the fundamental components of an inventive power supply circuit 20, as is demonstrated in detail in FIG. 2. The power-absorbing component 34 and the power-emitting component 36 can be embodied respectively as coils of a coil pair for an inductive power transfer or as a collector ring having a collector ring contact.

The X-ray detector 11 has a layer of a semiconductor-material 42, which is attached in such a way that X-ray radiation (not shown) generated by the X-ray source 14 (and optionally partially scattered and/or absorbed by an object positioned in the interior 43 of the ring mount 41) impinges on the semiconductor material 42. The semiconductor material 42 can be provided here in particular by cadmium telluride or cadmium zinc telluride, or also by a comparable semiconductor having similar relevant properties.

The semiconductor material 42 is connected to the bias voltage supply 5 in such a way that a bias voltage or bias UBias can be applied to the semiconductor material 42 by the bias voltage supply 5. In addition, the semiconductor material is thermally coupled to a heating element 45 and a cooling element 46. The heating element 45 is adapted to heat the semiconductor material 42 in order to increase themobility of free charge carriers there. Saturation of the defects in the semiconductor material 42 is facilitated hereby on the one hand and on the other hand the linearity for free charge carriers, which are generated in the semiconductor material 42 by X-ray radiation emitted by the X-ray source 14, is increased. The cooling element 46 is adapted to reduce the temperature of the semiconductor material 42 if it assumes a critical value as a consequence of incident X-ray radiation.

The power supply circuit 20 is connected to the X-ray source 14, the fan 16, the electronic control device 21 and the image processing 18 via the voltage supply 58 acting as a central current distributor, and can be connected to the heating element 45 and the cooling element 46 via the line 24 and via the bias voltage supply 5. In the operating state of the CT system 50 said components connected to the voltage supply draw their power supply through the power supply circuit 20 via the line 24.

The components directly connected to the voltage supply 58 acting as a central current distributor draw power only in the operating state. If the voltage supply 58 is interrupted because, for instance, the CT system 50 is to be put into sleep mode overnight, or a system restart is to take place, none of the components directly connected to the voltage supply 58 acting as a central current distributor is supplied with power. As already mentioned, in the case of a brief interruption to the voltage supply, it is possible to change over to an uninterruptible power supply, however. This procedure takes place in the manner demonstrated in FIG. 2 to FIG. 4.

To conclude, reference is made once more to the fact that the preceding apparatuses and methods described in detail are merely exemplary embodiments, which a person skilled in the art can modify in a wide variety of ways without departing from the scope of the invention. Furthermore, use of the indefinite article "a" or "an" does not preclude the relevant features from also being present multiple times. Similarly, the term "unit" does not preclude it from being composed of a plurality of components, which can optionally also be spatially distributed.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly"

on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A power supply circuit for a computed tomography system, the power supply circuit comprising:
   a stationary power distributor including an uninterruptible power supply;
   a co-rotating bias voltage supply, the co-rotating bias voltage supply including,
   a voltage supply input,
   a bias voltage supply output, and
   a bias voltage monitoring unit, the bias voltage monitoring unit being configured to activate or to deactivate the bias voltage supply output as a function of an electrical input voltage detected at the voltage supply input, and the bias voltage monitoring unit includes a sensor configured to detect the electrical input voltage at the voltage supply input; and
   an auxiliary voltage source having a power buffer, the power buffer configured to supply the bias voltage monitoring unit with electrical power for deactivation of the bias voltage supply output.

2. The power supply circuit of claim 1, wherein the bias voltage monitoring unit is configured to deactivate the bias voltage supply output in response to the sensor detecting the electrical input voltage undershoots a predetermined threshold voltage, and activate the bias voltage supply output in response to the sensor detecting that the electrical input voltage overshoots the predetermined threshold voltage.

3. The power supply circuit of claim 2, wherein the bias voltage monitoring unit includes a non-volatile data memory storing information, the information indicating a duration the electrical input voltage undershoots a predetermined threshold voltage.

4. The power supply circuit of claim 3, wherein the bias voltage monitoring unit includes a time measuring unit, the time measuring unit configured to ascertain a duration the electrical input voltage undershoots a predetermined threshold value of an electrical voltage.

5. The power supply circuit of claim 4, wherein the time measuring unit includes a clock cycle counting unit, the clock cycle counting unit configured to ascertain the duration by counting clock cycles.

6. The power supply circuit of claim 1, wherein the bias voltage monitoring unit includes a non-volatile data memory storing information, the information indicating a duration the electrical input voltage undershoots a predetermined threshold voltage.

7. The power supply circuit of claim 6, wherein the bias voltage monitoring unit is configured to continue to ascertain the duration and to write a value of the duration into the non-volatile data memory as long as sufficient power is supplied by the power buffer when the electrical input voltage does not reach a predetermined threshold value before the duration reaches a predetermined maximum value.

8. The power supply circuit of claim 7, wherein the bias voltage monitoring unit includes a read-out unit, the read-out unit configured to read out a value of the duration to ascertain a power storage capacity of the power buffer.

9. The power supply circuit of claim 8, wherein the bias voltage monitoring unit is configured to delete the non-volatile data memory after the read out.

10. The power supply circuit of claim 1, wherein the bias voltage monitoring unit includes a time measuring unit, the time measuring unit configured to ascertain a duration the electrical input voltage undershoots a predetermined threshold value of an electrical voltage.

11. The power supply circuit of claim 10, wherein the time measuring unit includes a clock cycle counting unit, the clock cycle counting unit configured to ascertain the duration by counting clock cycles.

12. The power supply circuit of claim 10, wherein the bias voltage monitoring unit includes a write unit, the write unit configured to write the duration into a non-volatile data memory.

13. The power supply circuit of claim 12, wherein the bias voltage monitoring unit is configured to
activate the bias voltage supply output when the electrical input voltage reaches the predetermined threshold value of an electrical voltage before the duration reaches a predetermined maximum value, and activate a standard process for initializing and booting up the electrical bias voltage supply output when the input voltage does not reach the predetermined threshold value of an electrical voltage before the duration reaches a predetermined maximum value.

14. The power supply circuit of claim 13, wherein the standard process for initializing and booting up the electrical bias voltage supply output comprises a controlled booting up of the electrical bias voltage.

15. The power supply circuit of claim 10, wherein the bias voltage monitoring unit is configured to
activate the bias voltage supply output when the electrical input voltage reaches the predetermined threshold value of an electrical voltage before the duration reaches a predetermined maximum value, and activate a standard process for initializing and booting up the electrical bias voltage supply output when the input voltage does not reach the predetermined threshold value of an electrical voltage before the duration reaches a predetermined maximum value.

16. The power supply circuit of claim 15, wherein the standard process for initializing and booting up the electrical bias voltage supply output comprises a controlled booting up of the electrical bias voltage.

17. The power supply circuit of claim 16, wherein the bias voltage monitoring unit is configured to continue to ascertain the duration and to write a value of the duration into a non-volatile data memory as long as sufficient power is supplied by the power buffer when the electrical input voltage does not reach a predetermined threshold value before the duration reaches a predetermined maximum value.

18. The power supply circuit of claim 1, wherein the power buffer comprises an electrical capacitor as a power storage unit.

19. A computed tomography system, having:
a scanning unit configured to acquire raw data from a patient with a semiconductor detector;
a control facility for actuating the scanning unit; and
the power supply circuit of claim 1.

20. A method for operating a computed tomography system, the method comprising:
detecting an electrical input voltage at a voltage supply input of a co-rotating bias voltage supply of the computed tomography system by a bias voltage monitoring unit;
activating or deactivating a bias voltage supply output of the bias voltage supply as a function of the electrical input voltage detected at the voltage supply input; and
supplying the bias voltage monitoring unit with electrical power by an auxiliary voltage source having a power buffer for the deactivating of the bias voltage supply output.

* * * * *